US006001087A

United States Patent [19]

Zurcher

[11] Patent Number: 6,001,087

[45] Date of Patent: *Dec. 14, 1999

[54] COLLECTION ASSEMBLY WITH A RESERVOIR

[75] Inventor: Robert G. Zurcher, Little Falls, N.J.

[73] Assignee: Becton Dickinson and Company, Franklin Lakes, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/724,559

[22] Filed: Sep. 30, 1996

[51] Int. Cl.[6] ........ A61B 19/00

[52] U.S. Cl. ........ 604/411; 604/403; 604/415; 600/573; 600/576

[58] Field of Search ........ 604/403, 407, 604/411, 415, 408; 128/760, 763, 764; 215/248, 247, 249, 250, 47, 48, 50; 600/573, 576, 577, 583

[56] References Cited

U.S. PATENT DOCUMENTS

| | | | |
|---|---|---|---|
| 2,449,968 | 9/1948 | Smith . | |
| 3,508,653 | 4/1970 | Coleman . | |
| 3,687,296 | 8/1972 | Spinosa et al. . | |
| 3,779,383 | 12/1973 | Ayres . | |
| 3,901,219 | 8/1975 | Kay . | |
| 4,134,512 | 1/1979 | Nugent | 215/247 |
| 4,675,159 | 6/1987 | Al-Sioufi | 422/36 |
| 4,880,602 | 11/1989 | Al-Sioufi . | |
| 5,061,263 | 10/1991 | Yamazaki et al. | 604/403 |
| 5,232,111 | 8/1993 | Burns | 604/403 |
| 5,246,434 | 9/1993 | Ebara | 604/403 |
| 5,306,270 | 4/1994 | Macartney et al. | 128/760 |
| 5,439,450 | 8/1995 | Haedt | 128/760 |
| 5,458,113 | 10/1995 | Burns | 128/763 |
| 5,511,558 | 4/1996 | Shepard et al. | 128/760 |
| 5,514,339 | 5/1996 | Leopardi et al. | 422/99 |
| 5,518,004 | 5/1996 | Schraga | 128/763 |
| 5,533,518 | 7/1996 | Vogler | 128/760 |
| 5,634,474 | 6/1997 | Grippi | 128/763 |
| 5,654,054 | 8/1997 | Trosha et al. | 128/764 |
| 5,725,832 | 3/1998 | Gundelsheimer | 600/573 |
| 5,738,670 | 4/1998 | Grippi . | |
| 5,803,284 | 9/1998 | Grimard | 215/249 |
| 5,817,082 | 10/1998 | Niedospial, Jr. et al. | 604/414 |

*Primary Examiner*—Corrine McDermott
*Assistant Examiner*—David J. Cho
*Attorney, Agent, or Firm*—Nanette S. Thomas, Esq.

[57] ABSTRACT

An assembly and method for storing and dispensing additives that are used in the preservation, separation or analysis of a blood sample. The assembly comprises a container, a reservoir and a cap wherein the reservoir is a liquid impermeable material.

9 Claims, 6 Drawing Sheets

COLLECTION ASSEMBLY WITH A RESERVOIR

BACKGROUND OF THE INVENTION

1. Field of the Invention

This invention relates to a collection assembly, and more particularly, relates to an assembly and method for storing and dispensing additives that are used in preservation, separation or analysis of a blood sample.

2. Description of the Related Art

Blood samples are routinely taken in evacuated tubes. One end of a double-ended needle is inserted into a patient's vein. The other end of the needle then punctures a septum covering the open end of the tube so that the vacuum in the tube draws the blood sample through the needle into the tube. Using this technique, a plurality of samples can be taken using a single needle puncture of the skin.

Collection tubes are conventionally made of glass or plastic. Glass tubes have the advantage of liquid and gas impermeability. Plastic tubes are advantageous over glass in lower breakage, less weight in shipment and easier disposal by insertion, but high permeability to liquid and gas is a disadvantage. For example, polyethylene-terephthalate (PET), though widely used commercially for blood collection, has a limited shelf life due to water permeability.

Blood drawn into a tube is typically mixed with an additive present in the tube prior to draw. Clot activators such as silica particles promote rapid coagulation so that the liquid serum fraction can be readily separated from the clotted cells. Anticoagulants, such as citric acid, heparin or ethylenediamentetraacetic acid (EDTA) are used to prevent clotting when the blood sample is to be used directly in hematological tests or to separate blood cells from the plasma.

The additive, whether procoagulant for clot activation or anticoagulant for clotting inhibition must be rapidly and thoroughly mixed with the blood sample to achieve its end use functionality. If the additive is present in the plastic tube as a solution, water absorption or transmission through the tube must be eliminated to prevent inaccurate additive concentrations. Additives in solution require precise concentrations to obtain reliable tube-to-tube performance.

Therefore, a need exists in the art of blood collection for a means of accurate storage and dispensing of tube additives that reduces dependence on phlebotomist technique and permits use of different plastics for tube manufacture.

SUMMARY OF THE INVENTION

The present invention is a collection assembly comprising a container and a cap and means for containing and dispensing an additive into the container.

The container preferably comprises a top portion, a closed bottom portion, a sidewall extending from the top portion to the bottom portion and an open end associated with the top portion. The cap preferably comprises a top portion with a puncturable stopper material therein, a bottom portion and an annular skirt extending from the top portion to the bottom portion wherein the annular skirt has an inner surface and an outer surface. The means for containing and dispensing an additive is a reservoir. The reservoir is located at the open end of the container in the top portion. Most preferably, the cap is placed over the reservoir and the container. The material of the reservoir is most preferably water impermeable and when a hollow needle punctures it, the additive contained in the reservoir is released into the container.

Thus, the additive may be precisely measured and stored in the water impermeable reservoir whereby substantial concentration changes of the additive are minimized. Further, the additive is thoroughly mixed with the blood during draw and completely washed in the container in a procedure independent of phlebotomist technique.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood collection assembly of the invention may include any container having a closed end an open end. Suitable containers are, for example bottles, vials, flasks and the like. Most preferably, the container is a tube.

Figure 1:
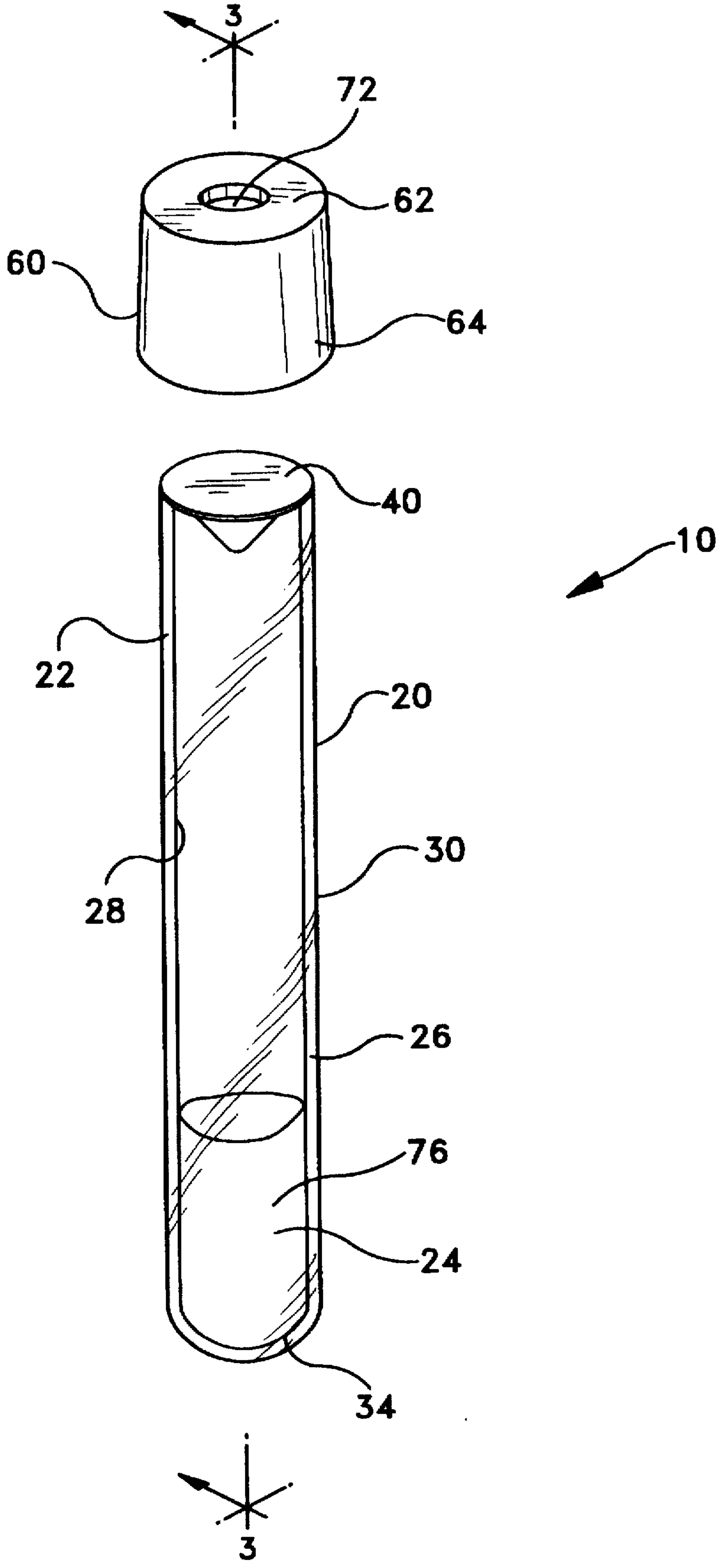
FIG. 1 is a perspective view of the preferred collection assembly illustrating the container, the reservoir and the cap exploded away.
Figure 2:
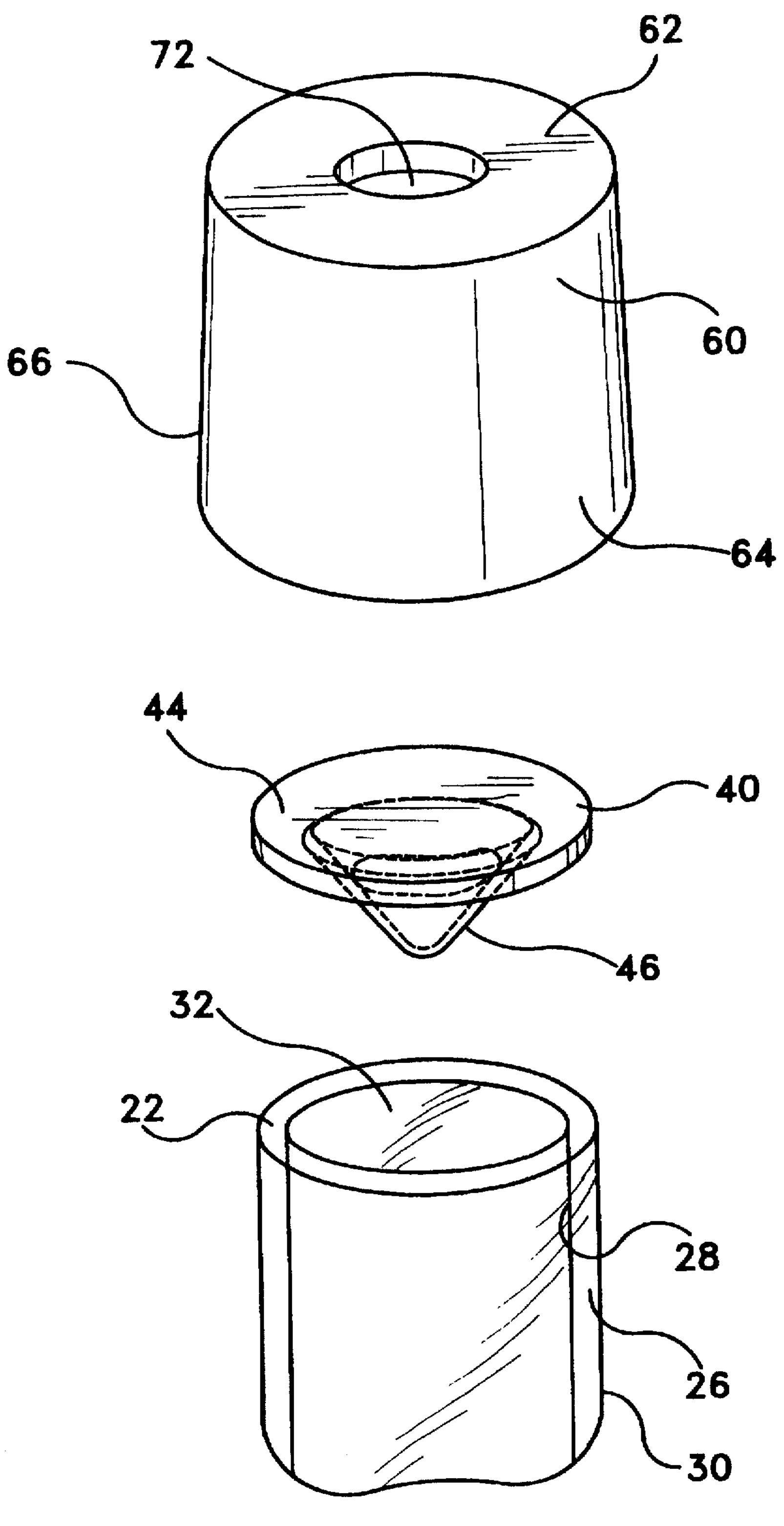
FIG. 2 is an exploded view of the top portion of the container, the reservoir and the cap.

FIG. 1 illustrates a blood collection tube assembly 10 which includes a tube 20, a reservoir 40 and a cap 60. As shown in FIGS. 1–2, tube 20 has a top end 22, bottom end 24 and sidewall 26 that extends between top end 22 and bottom end 24. Sidewall 26 has an inside wall surface 28 and an outside wall surface 30 and top end 22 has an open end 32 and bottom end 24 has a closed end 34.

Figure 3:
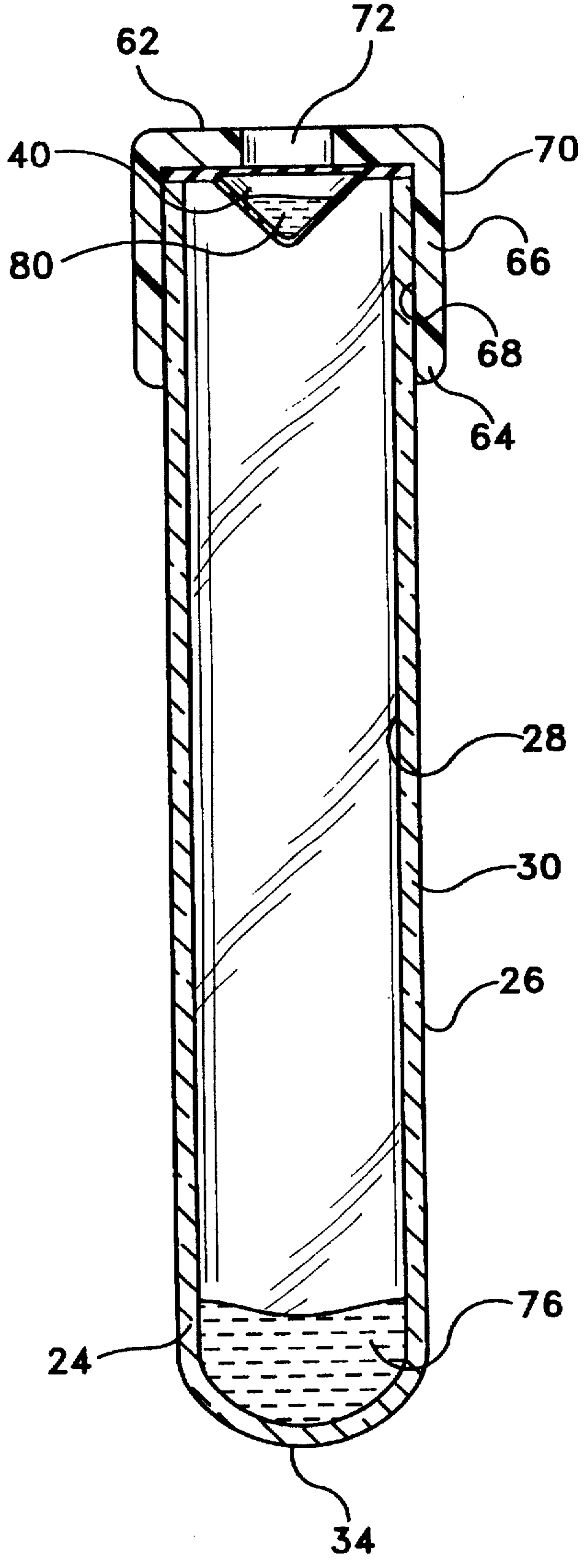
FIG. 3 is a side sectional view of the assembly of FIG. 1 taken along 3—3 thereof.

Reservoir 40 provides the means for storing and delivering an additive 48 into the tube, and as shown in FIG. 3, reservoir 40 is located in open end 32 and adjacent with top end 22 of the tube. Reservoir 40 is one piece, a pouch having a top section 44, and a closed bottom section 46. Reservoir 40 is made of puncturable, non-resealable material. The reservoir is held in place by the cap or may optionally be securely attached by an adhesive to the top portion of the tube.

The reservoir is preferably made of a material which is water impermeable, non-reactive to any additive therein and is puncturable without being resealable. Suitable materials include, but are not limited to, liquid impermeable plastics such as polyolefin and polyvinyl chloride or metals such as foil.

As shown in FIG. 3, cap 60 has an upper portion 62 which extends over reservoir 40 and a annular skirt 66 that has an inner surface wall 68 and an outer surface wall 70. Annular skirt 66 extends from upper portion 62 towards lower portion 64 wherein inner surface wall 68 presses against the outside wall surface 30 of the tube so as to keep the cap in place. Also, the cap has a septum portion 72 in upper portion 62 for receiving a cannula therethrough. Septum portion is a natural or synthetic rubber, resilient plastic or elastomeric material that is puncturable and self-sealing material.

Most preferably, tube 20 is evacuated and reservoir 40 is not evacuated.

Optionally, tube 20 may contain a conventional serum separating gel 76 as shown in FIG. 1.

Any additive 80 useful in blood preservation, storage or analysis, including both procoaugulants and anticoagulants may be stored in the reservoir.

When blood analysis is performed on serum, procoagulants are often used to enhance the rate of clotting. Such procoagulants which may be stored in the reservoir are particulate clot activators including but not limited to silica particles or enzyme clot activators such as elagic acid, fibrinogen and thrombin.

When blood analysis is performed on plasma, an anticoagulant is used to inhibit coagulation while blood cells are removed by centrifugation. Such anticoagulants include for example, chelators such as oxalates, citrate and EDTA or enzymes such as heparin.

The additives may be supplied in the reservoir in any desired form, such as a solution in a solvent or wetting agent. A preferable solvent is water or saline. Another desirable form of the additive is powered, crystalline or lyophilized solid.

When the reservoir is fully pierced by the cannula, blood draw is initiated by the reduced pressure in the evacuated tube. Blood flow continues upon retraction of the cannula so that the blood is delivered from the cannula directly into the interior volume of the reservoir where it contacts the additive. A vigorous and vortex mixing of the additive and blood in the reservoir is established. If the additive is soluble, such as citrate, it dissolves in blood; if it is insoluble, such as silica particles, it becomes suspended in the blood. The blood-additive mixture is drawn from the reservoir by the pressure differential between the tube and the reservoir. Therefore, due to the pressure differential, the blood and additive flow into the tube.

Figure 4:
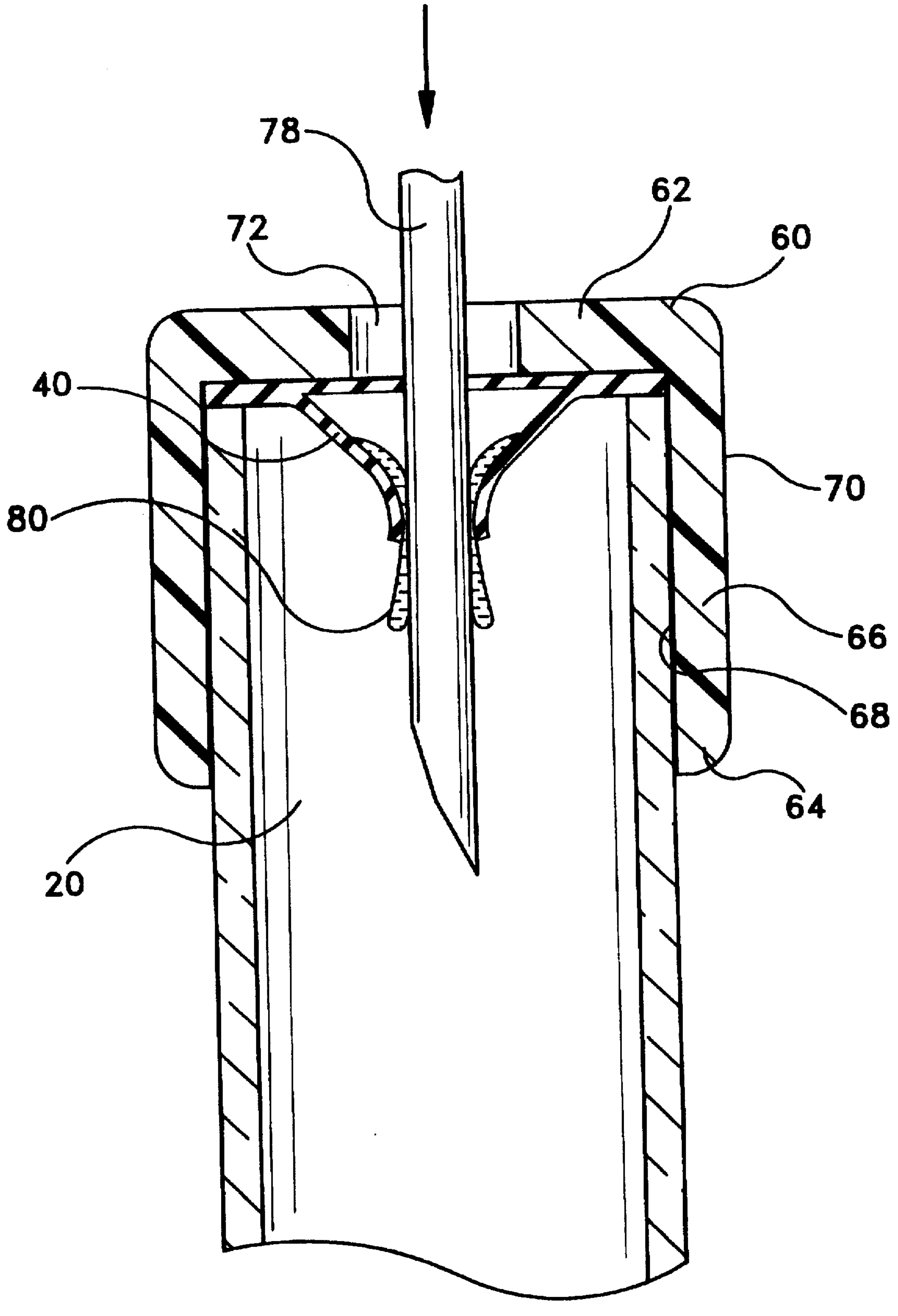
FIG. 4 is an enlarged partial sectional view of the assembly of the present invention of FIG. 1 showing the puncture of the cap and reservoir by a cannula.
Figure 5:
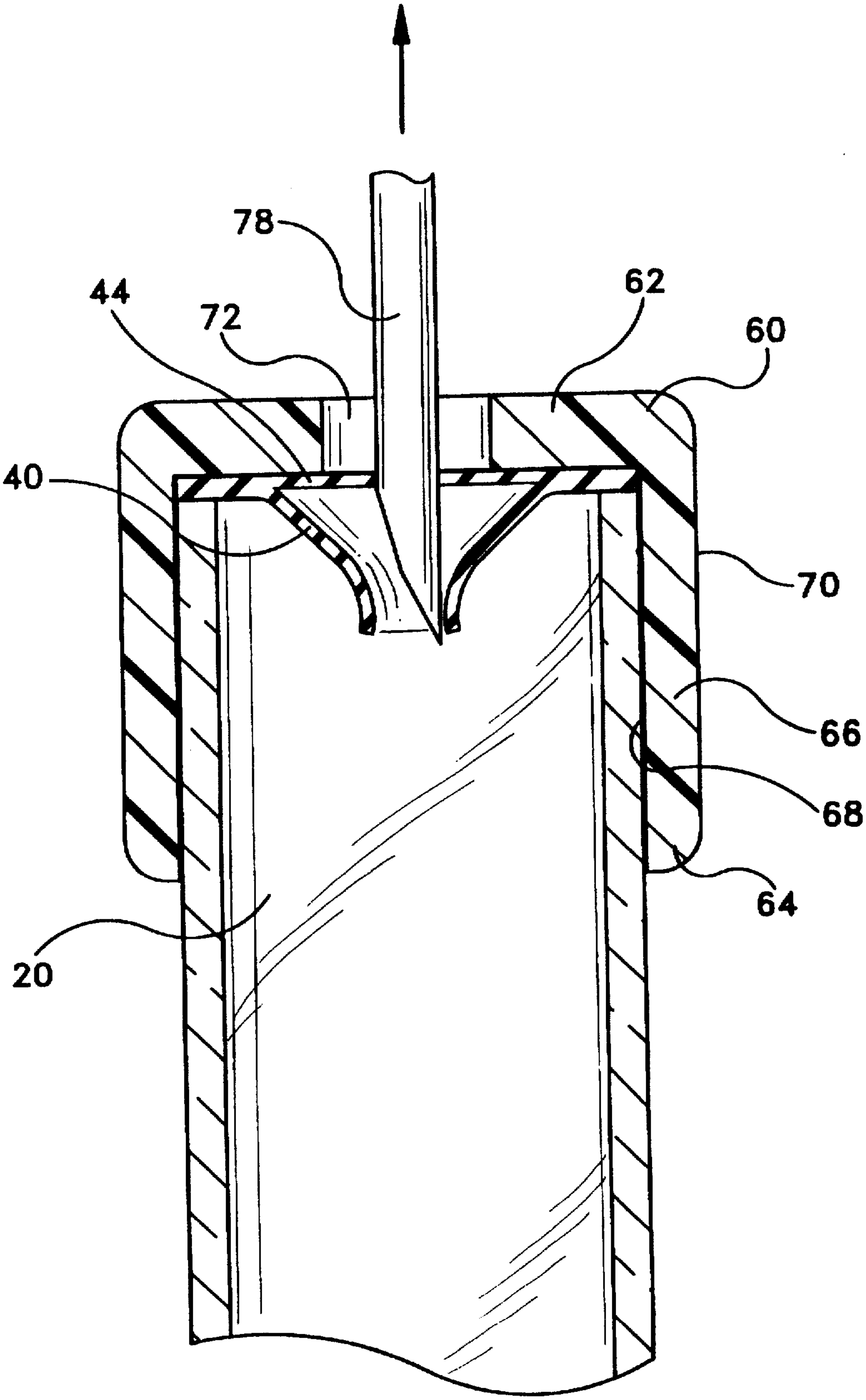
FIG. 5 shows after the cannula of FIG. 5 has been partially withdrawn to reside within the assembly.

In use, the septum portion of the cap is pierced by a cannula 78 during blood sampling. FIGS. 4 and 5 illustrate use of the present invention during blood sampling. In FIG. 4, one end of a cannula is connected to a blood supply such as a patient's vein (not shown in the drawing) and the other end is inserted by puncture through the septum and completely through the reservoir. When the cannula has completely punctured the reservoir, both top section 44 and closed bottom section 46, cannula is partially retracted to reside within the reservoir. FIG. 4 shows cannula 78 within reservoir 40. After puncture, and because the reservoir is non-resealable, the reservoir has two holes therein, though which additive is conveyed by the blood sample into the tube.

Puncture and partial retraction of the cannula may easily be performed manually or alternatively may be performed with a spring loaded needle holder which automatically determines the length of cannula insertion for puncture and the length of cannula retraction into the reservoir.

Figure 6:
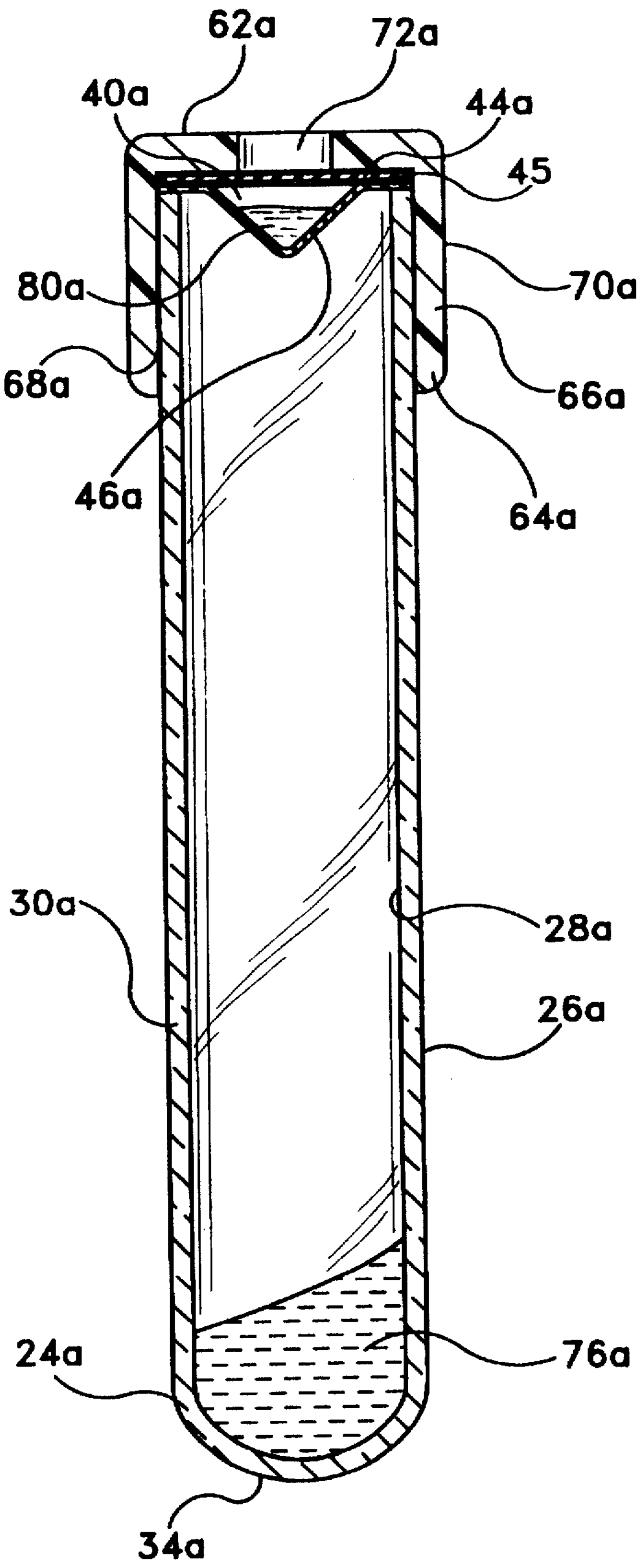
FIG. 6 is a side sectional view of the assembly similar to FIGS. 1 and 3, illustrating an additional embodiment of the invention wherein the reservoir is constructed in two pieces.

An additional embodiment of the invention, as shown in FIG. 6 includes many components which are substantially identical to the components of FIGS. 1–5. Accordingly, similar components performing similar functions will be numbered identically to those components of FIGS. 1–5, except that a suffix "a" will be used to identify these similar components in FIG. 6.

FIG. 6 shows an alternate embodiment of the invention, a blood collection tube assembly **10*a* which includes a tube 20*a*, a reservoir 40*a* and a cap 60*a*. As shown in FIG. 6, the alternate embodiment of the invention comprises a reservoir 40*a* that includes a top section 44*a*, a closed bottom section 46*a* and an adhesive 45 to secure top section 44*a* and closed bottom section 46*a*** together.

The tube may be made of glass or preferably plastic. Suitable plastics include but are not limited to, polypropylene (PP), polyethylene terephthalate (PET) and polystyrene (PS).

What is claimed is:

1. A blood collection assembly comprising:
   - a container having a top portion, a closed bottom portion, a side wall extending from said top portion to said closed bottom portion and an open end associated with said top portion;
   - a reservoir comprising a top portion and closed bottom portion for dispensing an additive into said container and attached to said open end of said top portion of said container with an adhesive material; and
   - a cap associated with said top portion of said container and said reservoir, said cap comprising an upper portion, a lower portion, and an annular skirt extending from said upper portion of said cap to said lower portion of said cap, said annular skirt having an inner surface wall and an outer surface wall, and said cap having a puncturable stopper material in said upper portion.

2. The blood collection assembly of claim 1 wherein said reservoir comprises an additive for use in analysis of blood.

3. The blood collection assembly of claim 1 wherein said reservoir is made of a liquid impermeable material.

4. The blood collection assembly of claim 3 wherein said reservoir is made of polyolefin, polyvinyl chloride or metal.

5. The blood collection assembly of claim 1 wherein said additives are anticoagulants or procoagulants.

6. The blood collection assembly of claim 5 wherein said additives further comprise a solvent or wetting agent.

7. A method for preparing a blood sample for analysis, using the assembly of claim 1, comprising:
   - a. puncturing said cap and said reservoir with a first end of a double ended cannula, a second end of said cannula being in fluid communication with a blood sample to be analyzed, said puncturing defining a hole in said reservoir;
   - b. retracing said cannula through said hole but not through said cap whereby blood is d&awn by a pressure differential into said container; and
   - c. allowing the blood drawn into said container to contact the additive in the reservoir so that said blood and said additive flow through said hole into said container.

8. The method for preparing a blood sample for analysis of claim 7, further comprising vigorous and vortex mixing of said additive and said blood in said reservoir when said reservoir is pierced by said cannula and said blood allowed to contact said additive.

9. The blood collection assembly of claim 1, wherein said reservoir is a unitary pouch.

* * * * *